(12) United States Patent
Roessiger

(10) Patent No.: US 9,885,676 B2
(45) Date of Patent: Feb. 6, 2018

(54) METHOD FOR THE MEASUREMENT OF A MEASUREMENT OBJECT BY MEANS OF X-RAY FLUORESCENCE

(71) Applicant: Helmut Fischer GmbH Institut fur Elektronik und Messtechnik, Sindelfingen (DE)

(72) Inventor: Volker Roessiger

(73) Assignee: Helmut Fischer GmbH Institut für Elektronik und Messtechnik, Singelfingen (DE)

( * ) Notice: Subject to any disclaimer, the term of this patent is extended or adjusted under 35 U.S.C. 154(b) by 101 days.

(21) Appl. No.: 14/634,979

(22) Filed: Mar. 2, 2015

(65) Prior Publication Data

US 2015/0247812 A1    Sep. 3, 2015

(30) Foreign Application Priority Data

Feb. 28, 2014   (DE) .................. 10 2014 102 684

(51) Int. Cl.
  *G01N 23/223*   (2006.01)
  *G01B 15/02*   (2006.01)

(52) U.S. Cl.
  CPC .......... *G01N 23/223* (2013.01); *G01B 15/02* (2013.01); *G01N 2223/076* (2013.01); *G01N 2223/6113* (2013.01); *G01N 2223/633* (2013.01)

(58) Field of Classification Search
  CPC ............. G01N 23/223; G01N 2223/61; G01N 2223/6113; G01N 2223/076; G01N 2223/633; G01B 15/02
  See application file for complete search history.

(56) References Cited

U.S. PATENT DOCUMENTS 5,541,973 A * 7/1996 Tamura ................. G01N 23/22
  378/45
6,364,528 B1 * 4/2002 Rossiger .............. G01N 23/223
  378/207

(Continued)

FOREIGN PATENT DOCUMENTS

DE    198 36 884 C1   6/2000
JP    H07-128 259 A   5/1995

(Continued)

*Primary Examiner* — David J Makiya
*Assistant Examiner* — Soorena Kefayati
(74) *Attorney, Agent, or Firm* — Renner, Otto, Boisselle & Sklar, LLP

(57) ABSTRACT

A method for measurement of the thickness of thin layers or determination of an element concentration of a measurement object. A primary beam is directed from an X-ray radiation source onto the measurement object. A secondary radiation emitted by the measurement object is detected by a detector and is relayed to an evaluation device. The primary beam is moved within a grid surface which is divided into grid partial surfaces as well as subdivided into at least one line and at least one column. For each grid partial surface a primary beam is directed onto the grid surface. A measuring spot of the primary beam fills at least the grid point. A lateral dimension of the measurement surface is detected and compared to the size of the measuring spot of the primary beam appearing on the measurement object, for size determination of the measurement surface of the measurement object.

9 Claims, 4 Drawing Sheets

(56) References Cited

U.S. PATENT DOCUMENTS

Figure 1:
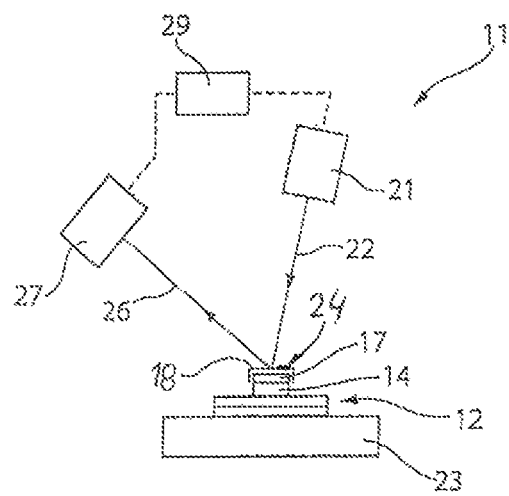

| | | | | |
|---|---|---|---|---|
| 6,370,221 | B2* | 4/2002 | Kaiser | G01N 23/223 |
| | | | | 378/150 |
| 6,885,727 | B2* | 4/2005 | Tamura | G01N 23/20 |
| | | | | 378/45 |
| 7,653,174 | B2* | 1/2010 | Mazor | G01N 23/223 |
| | | | | 378/50 |
| 8,625,737 | B2* | 1/2014 | Chen | G01N 23/12 |
| | | | | 378/208 |
| 8,644,450 | B2* | 2/2014 | Kita | G01N 23/223 |
| | | | | 378/44 |
| 9,188,552 | B2* | 11/2015 | Kinugasa | G01T 1/17 |
| 9,194,829 | B2* | 11/2015 | Smith | G01N 23/2252 |
| 9,389,192 | B2* | 7/2016 | Tokar | G01N 23/223 |
| 9,535,018 | B2* | 1/2017 | Peterlinz | G01B 15/00 |
| 2012/0097848 | A1* | 4/2012 | Lifshin | G02B 21/002 |
| | | | | 250/307 |
| 2013/0039460 | A1* | 2/2013 | Levy | G01N 21/211 |
| | | | | 378/44 |

FOREIGN PATENT DOCUMENTS

| | | |
|---|---|---|
| JP | H07-270 346 A | 10/1995 |
| JP | 2004-003 959 A | 1/2004 |

* cited by examiner

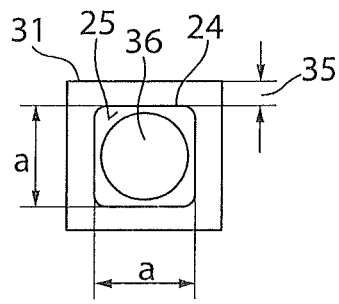
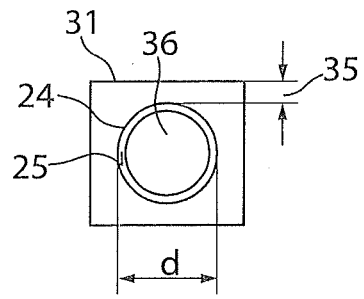
Fig. 3a Fig. 3b
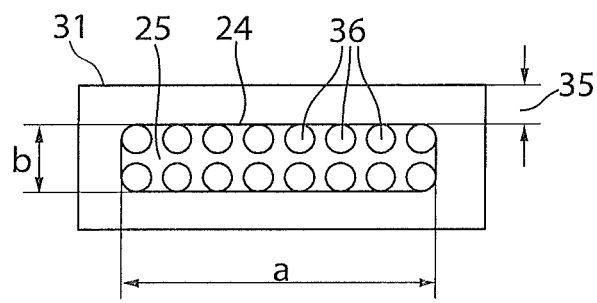
Fig. 3c
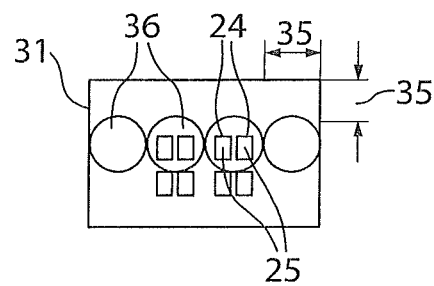
Fig. 3d

METHOD FOR THE MEASUREMENT OF A MEASUREMENT OBJECT BY MEANS OF X-RAY FLUORESCENCE

This application claims priority of German Application No. 10 2014 102 684.5 filed Feb. 28, 2014, which is hereby incorporated herein by reference.

The invention relates to a method for the measurement of a measurement object by means of X-ray fluorescence, in particular for the measurement of a thickness and element composition of thin layers of a measurement object.

In many areas of industrial manufacturing, increasingly small structures are used, such as, for example, so-called bond pads of circuit boards. Such small structures often have a coating. In these cases, it is continually required to analyse the coating, in particular to determine the layer thickness thereof.

To determine the layer thickness and analyse the coating, it is generally known to use an X-ray fluorescence method. Therein a primary beam is directed from a source of radiation to the measurement object. A secondary radiation emitted by the measurement surface is detected by a detector and relayed to the evaluation device, in order to determine, for example, the layer thickness. Therein the size of the primary beam is adapted to the structural size of the measurement object, wherein the measurement of small structures then finds its limit if the stimulating primary beam is larger in its lateral dimension than the flat surface of the measurement object. This means that the smaller the measurement object is, the smaller the measuring spot of the primary beam must be. This could occur by fading out the stimulating beam of the primary beam, whereby, however, a reduction of the intensity and thus an impairment in the detection of the spectrum of the secondary radiation emerge. There are thus limits for this conventional technique.

Therefore it is known to provide polycapillary optics, in particular a polycapillary lens, between a radiation source and the measurement object, using which the intensity can be increased in a small measuring spot. This has the disadvantage, however, that the spatial distribution of the radiation intensity is out of focus. Therefore, until now, small structures with a measuring spot of only up to approx. 60 µm are able to be detected. Additionally, such polycapillaries are very expensive.

Smaller measuring spots for the measurement of structures having a measurement surface of smaller than approximately 60 µm can be generated only with the aid of so-called monocapillaries. However, here the achievable intensity is so low that these are not considered for the technical application.

The object of the invention is therefore to enable a method for the measurement of measurement objects having smaller dimensions, in particular in a cost-effective manner.

This object is solved according to the invention by a method by means of X-ray fluorescence, in which a size of the measurement surface of the measurement object is detected, and as a result the size of the measuring spot of the measurement object is compared to a size of a measuring spot of the primary beam appearing at the measurement object and for the determination of a measurement surface which is smaller than the measuring spot, a size of the grid surface is selected which at least covers the measurement surface of the measurement object, wherein a scaling factor $\alpha$ is determined from the ratio of the grid surface to the surface of the measurement object, said scaling factor $\alpha$ being multiplied by the detected spectra of the individual measurements of the respective grid partial surfaces after the adding up and the averaging thereof and subsequently the spectrum that is corrected with the scaling factor $\alpha$ is provided for quantitative evaluation. Using this method it is possible to measure the measurement surfaces of the measurement object, the measurement surface of which is smaller than the measuring spot of the primary beam appearing on the measurement surface. Using the determination of a spectrum of the secondary radiation of each grid partial surface within a grid surface as well as the adding up and averaging of the spectra and the subsequent correction with the scaling factor $\alpha$, it is possible that the limitation and/or the spatial resolution properties of the X-ray optics must not be known exactly and nevertheless reliable measurement results are enabled. Thus also a detection of a measurement surface of the measurement object which lies only partially inside a grid partial surface, influences the evaluation such that, due to the ratio formation of the size of the grid surface to the size of the measurement surface, a scaling factor $\alpha$ serves as a correction factor in order to evaluate the individual determined spectra of the secondary radiation inside the grid partial surfaces of the grid surface.

Preferably the spacing of the grid partial surface is determined by the size of the measuring spot of the primary beam, which appears on the measurement object. Thus additional adjustment or change of optics is not required. Rather the size of the measuring spot is determined in a device-specific manner for X-ray fluorescence measurement devices such that a size that is verified on the side of the device is thus specified which is used for the method.

Furthermore, preferably the size of the grid surface is formed from an integer multiple of measuring spots of the primary beam which are lined up directly on top of one another or overlapping. A grid surface having only one line or one column can be formed from several measuring spots lined up next to one another or on top of one another. A matrix can be provided made from both the same and a different number of lines and columns having any measuring spots lined up on top of one another. This grid surface can be adapted to the measurement object or to the contour of the measurement surface of the measurement subject. In any case, each grid partial surface is at least filled by one measuring spot.

The corrected spectra of the secondary radiation from the individual measurements of the grid partial surfaces are preferably evaluated by means of evaluation software such that from this an element concentration or layer thickness of the coating or a layer on a base material is determined and emitted. Thus a simple check can occur as to whether a coating on a base material is sufficient with regard to the layer thickness and/or sufficient with regard to the individual element concentrations.

A further advantageous embodiment of the method provides that a travel distance from grid partial surface to grid partial surface within a line or a column or from a line or column into the next column or line within the grid surface is determined by the size of the measuring spot of the primary beam of the radiation sources. The measuring spot of the primary beam is determined by a so-called primary spot on an anode of the X-ray tube. Due to the travel distance from grid partial surface to grid partial surface, the grid surface can be completely detected with regard to the entire surface, such that transitions can be detected with regard to presence and non-presence of layers to be measured.

Furthermore, preferably the size of the measurement surface of the measurement object is determined by an optical measurement method. Thus, in a simple manner, an exact determination can be enabled in order to use this size of the measurement surface as a basis for the determination of the scaling factor.

Advantageously, the size of the grid surface is determined to be larger than the determined measurement surface of the measurement object, wherein the grid surface surrounds the determined measurement surface at least in sections at least partially from one edge. This edge serves to specify at least one transition from a region that is not to be detected and the measurement surface of the measurement object in order to detect and to take into account an intensity change.

The edge that at least partially surrounds the measurement surface of the measurement object has a width of at least one size of a grid partial surface. In the case of a rectangular or square measurement surface, the grid surface is larger than the measurement surface by at least two grid partial surfaces such that an edge is formed on each side edge. Advantageously, a grid partial surface has the size of a so-called full width at half maximum (FWHM) which are specific for each X-ray fluorescence device.

Figure 2:
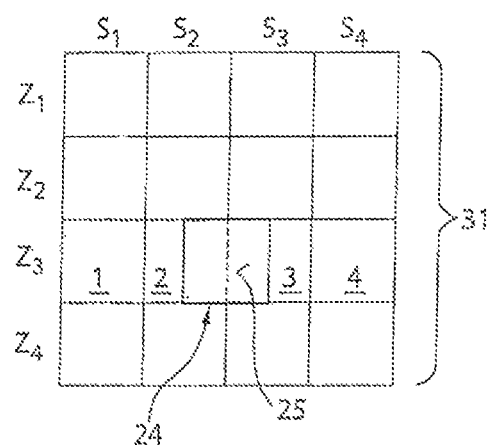
Figure 4:
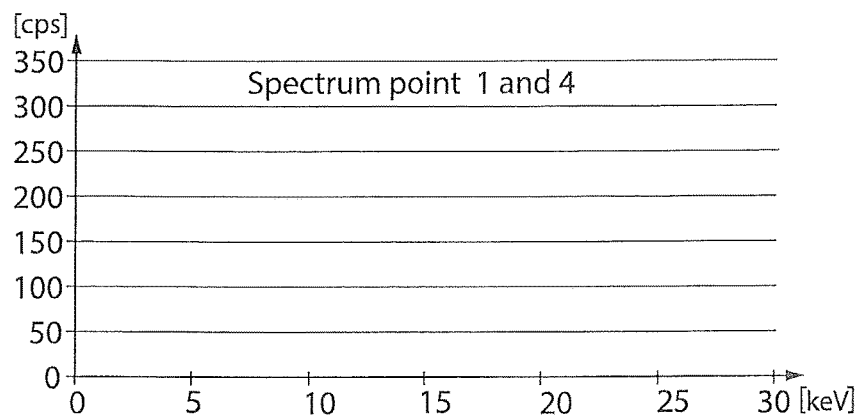
Figure 9:
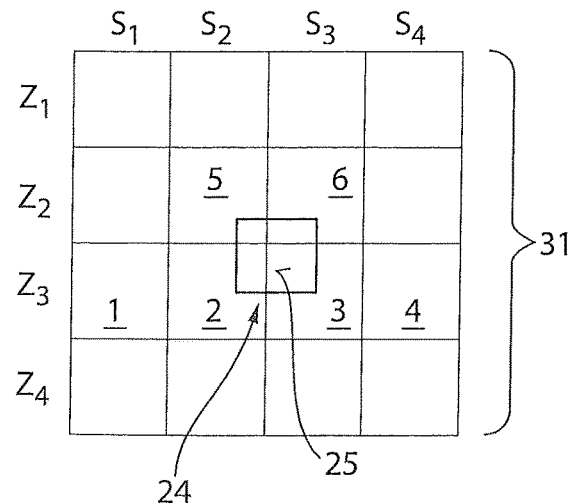

The invention as well as further advantageous embodiments and developments of the same are described and explained in more detail below by means of the examples depicted in the drawings. The features to be gleaned from the description and the drawings can be applied individually or together in any combination according to the invention. Herein are shown:

FIG. 1 a schematic view of a device to implement an X-ray fluorescence analysis, FIG. 2 a schematically enlarged view of a measurement surface of a measurement object having an associated grid surface, FIGS. 3a and 3d schematic views to determine a size of a grid surface for different geometries of the measurement surface, FIGS. 4 to 8 diagrams with regard to measurement values and a quantitative evaluation resulting from this and FIG. 9 a schematically enlarged view of a measurement surface of a further measurement object having a grid surface arranged thereon.

In FIG. 1, a device 11 for the implementation of an X-ray fluorescence analysis having a specimen 12 is depicted schematically. This can be, for example, a circuit board having bond pads. For example, the bond pad can consist of a thin copper bar 14 on a circuit board. A nickel layer 17 is applied to the copper bar 14, said nickel layer 17 being covered with a gold layer 18 to prevent corrosion. At least the gold layer 18 and for the most part also the nickel layer 17 must be measured and checked, in the case of such an embodiment, with regard to the layer thickness and the element concentrations.

This device 11 comprises an X-ray radiation source 21 or an X-ray tube, via which a primary radiation 22 is emitted and is directed to the specimen 12 which can be received, for example, by a specimen carrier 23. The specimen carrier 23 can be adjusted in position and/or in height, preferably by means of a driveable table, which in particular is driven by a motor. The primary beam 22 can, for example, be focused via a collimator which is not depicted in more detail here. The primary beam 22 is directed onto a measurement object 24 of the specimen 12, for example, perpendicularly or at an angle to the surface of the specimen 12 which deviates from this. Therein an X-ray fluorescence radiation is stimulated in the surface of the specimen 12, which is emitted as a secondary radiation 26 from the specimen 12 and is detected by a, preferably energy-dispersive, detector 27. An evaluation of the detected measurement results from the detector 27 occurs via an evaluation device 29 which evaluates and emits the detected signals of the detector 27.

In FIG. 2, a schematic view from above onto a measurement object 24 having a measurement surface 25 is depicted. The size of such a measurement object 24 can, for example, comprise a length and/or width of 60 µm or 50 µm or less.

For the implementation of a measurement of such a small measurement surface 25 of the measurement object 24, a grid surface 31 made from several grid partial surfaces 1, 2, 3, 4 . . . n is determined, which are arranged in lines Z1 . . . Zn and/or columns S1 . . . Sn. For the determination of the size of the grid surface 31, firstly an optical detection of the measurement surface 25 of the measurement object 24 occurs. For example, an optical measurement device, in particular a microscope or a scanning electron microscope, is used. Subsequently the grid surface 31 is determined. The optically determined size of the measurement surface 25 of the measurement object 24 is compared to a size of a measuring spot 36 of the primary beam 22 which appears at the measurement surface 25 of the measurement object 24. The size of the measuring spot 36 is specified usually as a full width at half maximum (FWHM). This size is device-specific and is determined by the primary spot, the beam optics and the geometry in the anode allocated to the radiation source. Provided that the size of the measuring spot 36 is smaller than that of the measurement surface 25, a grid surface 31 is determined which is larger than the measurement surface 25 and advantageously has an edge 35 which is depicted in the FIGS. 3a to 3c below for different geometries of the measurement surface 25.

For example, according to FIG. 3a, for a quadratic measurement surface 25 having an edge length a, a uniformly circumferential edge 35 is provided such that the grid surface 31 with regard to a side edge is composed of the edge length a of the measurement surface 25 and twice the edge 35. This applies analogously for an exemplary circular measurement surface 25 according to FIG. 3b, wherein instead of the edge length a, the diameter d is used as a basis in order to determine the size of the grid surface 31. In FIG. 3c, for example, a rectangular measurement surface 25 is depicted in which the length of the side edge a clearly deviates from the length of the side edge b. The circumferential edge 35 is formed, however, analogously to FIG. 3a, in order to determine the grid surface 31. In FIG. 3d, the measurement object 24 is smaller with its lateral dimension of the measurement surface 25 than the measuring spot 36. Additionally, the spacing of the measurement objects 24 is smaller than the size of the measuring spot 36. In such a case, several measurement objects 24 are combined to form a total measurement surface and additionally the circumferential edge 35 is formed analogously to FIG. 3a in order to determine the grid surface 31.

The width of the edge 35 is advantageously designed in such a way that this comprises the size of at least one measuring spot 36. Alternatively, the edge 35 can also be wider. The number of the individual grid partial surfaces within at least one line Z1 to Zn and/or at least one column S1 to Sn is determined, originating from the determined size of the measurement surface 25 and the doubled value of a measuring spot 36 for the right and left edge 35, wherein the number of grid partial surfaces results from an integer multiple of the size of the measuring spot 36, as this is depicted, by way of example, in FIG. 2. The spacing of the grid partial surfaces therein corresponds to the size of the measuring spot 36, such that a complete scanning of the grid surfaces 31 with the primary beam 22 is possible for the detection of the spectra of the secondary radiation 26 from the individual measurements.

Subsequently, individual measurements are implemented at the grid partial surfaces 1 . . . n. This is discussed by means of a simplified example in which only the line Z3 and not the entire grid surface 31 is considered.

Firstly the primary beam 22 is directed onto the grid partial surface 1, which is situated in the position Z3/S1 of the grid surface 31. Subsequently, the measurement object 24 is driven to the left by one column width such that the primary beam 22 appears on the grid partial surface 2. This is repeated until the grid partial surfaces 3 and 4 have been irradiated such that the respective spectrum is detected by means of the detector 27. From this results, for example, the spectrum depicted in FIG. 4, for the grid partial surfaces 1 and 4. As a measurement surface 25 of the measurement object 24 was not included for the grid partial surfaces 1 and 4, with regard to this no detection of measurement values and thus no output from signals occurs.

Figure 5:
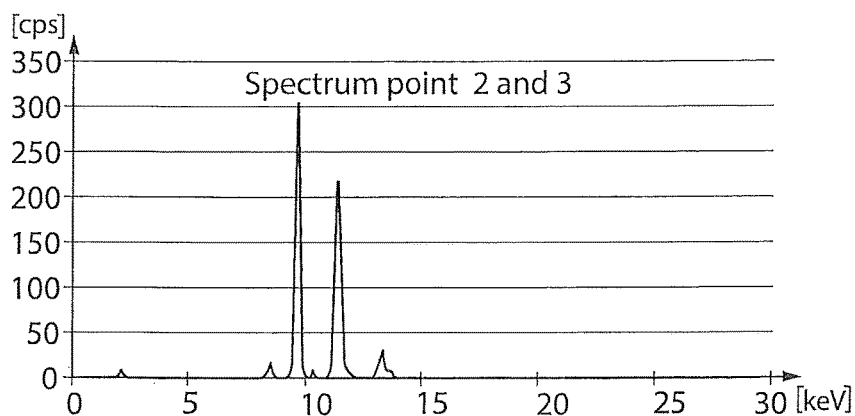
Figure 6:
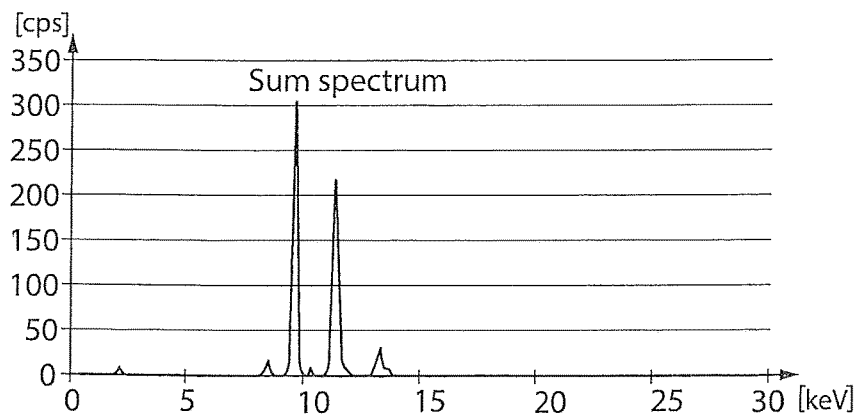

In FIG. 5, the spectrum of the grid partial surfaces 2 and 3 is depicted. As the grid partial surfaces 2 and 3 each cover a part of the measurement surface 25 of the measurement object 24, the thus determined spectrum is detected accordingly.

This exemplary detection of the spectra in the grid partial surfaces 1 to 4 in line 3 is implemented for all grid partial surfaces within the grid surface 31.

Instead of a line-by-line detection of the spectra, a column-by-column detection of the spectra of the secondary radiation 26 can also occur in the individual grid partial surfaces of the grid surface 31.

As a result, the detected spectra are evaluated in the respective grid partial surfaces of the grid surface 31. Firstly a sum spectrum is formed, which, in the example, consists of and is depicted to be made from the grid partial surfaces 1 to 4 in FIG. 6. This corresponds, in this case, to FIG. 5, as no spectrum was determined in the grid partial surfaces 1 and 4. Deviating from the exemplary case, if the entire grid surface were to be considered, a spectrum, which would be added up, would result from the points Z3/S2 and Z3/S3.

Figure 7:
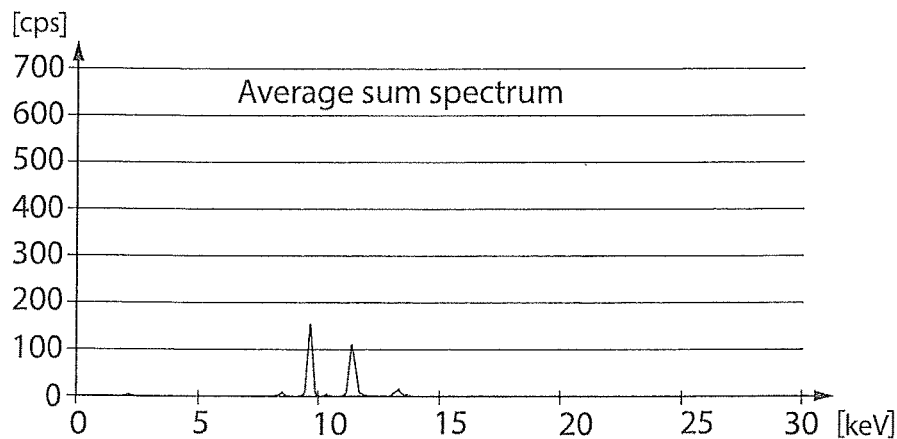
Figure 8:
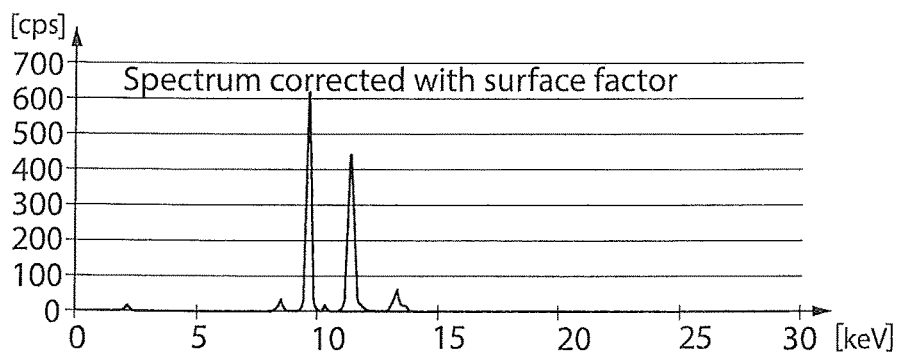

Subsequently, an average value is formed over the entire spectrum of the individual grid partial surfaces 1, which is depicted as an average sum spectrum in FIG. 7 for the grid partial surfaces 1 to 4. Subsequently, this average sum spectrum is corrected in that this is multiplied by the scaling factor $\alpha$. This scaling factor $\alpha$ results from the ratio of the size of the grid surface 31 to the size of the measurement surface 25. Subsequently, this spectrum which is corrected with the scaling factor $\alpha$ is provided in the evaluation device 29 for quantitative evaluation such that these determined values, for example, can be transferred into a layer thickness distribution profile or can be emitted into a layer thickness cross-sectional profile, from which the layer thicknesses and/or element concentrations are able to be read out or presented.

During the determination of the spectra at the grid partial surfaces 1 to 4, the measurement surface 25 of the measurement object 24 is driven by a motor by the amount of the measuring spot 36 or the grid partial surface, such that a direct sequencing of the individual measuring spots 36 is enabled. For this purpose, preferably a positioning table is provided which has such a resolution for the individual method steps, which corresponds to the size of the measurement surface 36.

For the embodiment according to FIG. 3d, the method referred to above applies, wherein this is, however, modified, such that two or more measurement objects 24 are combined into one total measurement surface in order to subsequently implement individual measurements at the grid partial surfaces. As a result, therein no statements can be made concerning the determined layer thickness or element concentration of the individual measurement objects 24, but rather an overall assessment of the measurement objects 24 from which an average value of the layer thickness or the element concentration for each measurement object 24 is deduced.

In FIG. 9, a practical example is depicted, as this appears most of the time, and deviates from FIG. 2 with regard to the positioning of the grid partial surfaces with respect to the lateral extension of the measurement object 24. For the implementation of the individual measurements, for example, the spectra determined in the grid partial surfaces 2, 3, 5 and 6 are combined and subsequently analysed analogously to the method described above.

The invention claimed is:

1. A method for the measurement of a measurement object by means of X-ray fluorescence, the method comprising:
    directing a primary beam from an X-ray radiation source onto the measurement object,
    using only a single detector to detect secondary radiation emitted from the measurement object and relaying the detected secondary radiation to an evaluation device, and
    moving the primary beam within a grid surface which is divided into grid partial surfaces as well as subdivided into at least one line and at least one column, the primary beam being directed onto the grid surface for each grid partial surface, with a measuring spot of the primary beam filling at least the grid partial surface,
    wherein a lateral dimension of the measurement surface of the measurement object is detected,
    wherein the lateral dimension of the measurement surface of the measurement object is compared to the size of the measuring spot of the primary beam appearing on the measuring object,
    wherein during the determination of the size of the measuring surface of the measurement object, which is smaller than the measuring spot, a size of the grid surface is selected which covers at least the measurement surface of the measurement object,
    wherein a scaling factor a is determined from a ratio of the size of the grid surface to the size of the measurement surface of the measurement object,
    wherein the detected spectrum of the secondary radiation is added up from the respective grid partial surfaces, averaged and subsequently multiplied by the scaling factor $\alpha$, and
    wherein the spectrum of the secondary radiation from the grid partial surfaces that is corrected with the scaling factor $\alpha$ is provided for quantitative evaluation.

2. The method according to claim 1, wherein the spacing of the grid partial surfaces is determined by the size of the measuring spot of the primary beam.

3. The method according to claim 1, wherein the size of the grid surface is formed from an integer multiple of measuring spots of the primary beam which are lined up directly on top of one another or overlapping.

4. The method according to claim 1, wherein element concentrations or layer thicknesses of the measurement object are determined from the spectrum of the individual measurements at the grid partial surfaces.

5. The method according to claim 1, wherein a travel distance of the measurement object from the one grid partial surface to the adjacent grid partial surface within a line or a column of the grid surface is determined by the size of the measuring spot of a primary beam of the radiation source.

6. The method according to claim 1, wherein a size of the measurement surface of the measurement object is determined by an optical measurement method.

7. The method according to claim 1, that for a distance between two measurement objects, which is smaller than the size of the measuring spot, two or more measurement objects are combined into one total measurement surface and a grid surface is determined for the total measurement surface and from this an average thickness of the thin layers or an average element concentration is deduced for the individual measurement object combined into the total measurement surface.

8. The method according to claim 6, wherein the size of the grid surface is designed to be larger than the determined measurement surface of the measurement object and is determined to be larger in such a way that the grid surface comprises the determined measurement surface and an edge which at least partially surrounds this.

9. The method according to claim 8, wherein the edge surrounding the measurement surface of the measurement object is determined at a width of the at least one size of the grid partial surface.

* * * * *